(12) United States Patent
Mumm et al.

(10) Patent No.: US 11,172,829 B2
(45) Date of Patent: Nov. 16, 2021

(54) THERMOACOUSTIC TRANSDUCER WITH INTEGRATED SWITCH

(71) Applicant: ENDRA Life Sciences Inc., Ann Arbor, MI (US)

(72) Inventors: Zackary Marc Mumm, Royal Oak, MI (US); Christopher Nelson Davis, Ann Arbor, MI (US); Michael M. Thornton, London (CA); Jang Hwan Cho, Ann Arbor, MI (US)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 17/230,480

(22) Filed: Apr. 14, 2021

(65) Prior Publication Data

US 2021/0321873 A1    Oct. 21, 2021

Related U.S. Application Data

(60) Provisional application No. 63/013,476, filed on Apr. 21, 2020.

(51) Int. Cl.
*A61B 5/00* (2006.01)
*G01N 29/24* (2006.01)
(Continued)

(52) U.S. Cl.
CPC .......... *A61B 5/0093* (2013.01); *A61B 5/0035* (2013.01); *A61B 5/05* (2013.01);
(Continued)

(58) Field of Classification Search
CPC ..... G01S 7/495; G01S 7/4876; G01S 7/52077
See application file for complete search history.

(56) References Cited

U.S. PATENT DOCUMENTS 10,888,898 B2    1/2021  Thornton et al.
2008/0269614 A1*  10/2008  Adachi ................ B06B 1/0292
                                                    600/459
(Continued)

OTHER PUBLICATIONS

Roggenbuck et al. "Volumetric Thermoacoustic Imaging over Large Fields of View". Ultrasonic Imaging, 35(1) 57-67, 2013 (Year: 2013).*

(Continued)

*Primary Examiner* — Joanne M Hoffman
*Assistant Examiner* — Milton Truong
(74) *Attorney, Agent, or Firm* — Stanley E. Jelic

(57) ABSTRACT

A thermoacoustic transducer integrating at least one piezoelectric element having a first surface and a second surface, a potential electrode that is electrically connected to the second surface, a ground electrode that is electrically connected to the first surface, a switch electrically connected to both the potential electrode and the ground electrode, a timer configured to match a pulse emanating from a radio-frequency emitter, further wherein the potential electrode and the ground electrode are electrically connected through an impedance when the switch is in an active state, further wherein the potential electrode and the ground electrode are not electrically connected when the switch is in an inactive state; and a housing accommodating the at least one piezoelectric element, potential electrode, ground electrode, and switch.

10 Claims, 5 Drawing Sheets

(51) Int. Cl.
  *A61B 5/05* (2021.01)
  *B06B 1/06* (2006.01)
(52) U.S. Cl.
  CPC .......... *A61B 5/7217* (2013.01); *A61B 5/7225* (2013.01); *B06B 1/0607* (2013.01); *G01N 29/2431* (2013.01)

(56) References Cited

U.S. PATENT DOCUMENTS

| | | | | |
|---|---|---|---|---|
| 2009/0001853 | A1* | 1/2009 | Adachi | B06B 1/0292 310/323.19 |
| 2012/0078109 | A1* | 3/2012 | Okuno | A61B 8/56 600/459 |
| 2012/0197117 | A1* | 8/2012 | Picot | A61B 5/415 600/438 |
| 2018/0156903 | A1* | 6/2018 | Pattipaka | A61B 8/4483 |
| 2018/0296187 | A1* | 10/2018 | Gomersall | A61B 8/4494 |
| 2019/0038220 | A1* | 2/2019 | Rubin | A61B 5/0035 |
| 2019/0307500 | A1* | 10/2019 | Byrd | A61B 18/1492 |
| 2020/0182989 | A1* | 6/2020 | Freeman | G01S 7/52095 |

OTHER PUBLICATIONS

Wenzheng Ding, Zhong Ji, Da Xing; Microwave-excited ultrasound and thermoacoustic dual imaging; Applied Physics Letters 110, 183701 (2017); pp. 1-4, published online May 5, 2017.

Konstantinos Marakakis, Georgios K. Tairidis, Panagiotis Koutsianitis, Georgios E. Stavroulakis; Shunt Piezoelectric Systems for Noise and Vibration Control; Frontiers in Built Environment | www.frontiersin.org; May 2019 | vol. 5 | Article 64; pp. 1-15; published: May 15, 2019 doi: 10.3389/fbuil.2019.00064.

Stephan Kellnberger, Murad Omar, George Sergiadis, Vasilis Ntziachristos; Second harmonic acoustic responses induced in matter by quasi continuous radiofrequency fields; Applied Physics Letters 103, 153706 (2013); pp. 1-4; published online Oct. 11, 2013.

* cited by examiner

THERMOACOUSTIC TRANSDUCER WITH INTEGRATED SWITCH

CROSS-REFERENCE TO RELATED APPLICATIONS

This application claims the benefit of U.S. Provisional Patent Application No. 63/013,476, filed on Apr. 21, 2020, the entirety of which is incorporated herein by reference.

FIELD

The subject application relates generally to thermoacoustic transducers and in particular, to a thermoacoustic transducer with an integrated switch configured to activate or deactivate as a radio-frequency device emits energy.

BACKGROUND

Thermoacoustic imaging systems typically comprise a thermoacoustic transducer encased in a housing. The thermoacoustic transducer may comprise a single piezoelectric element or an array of piezoelectric elements. A radio-frequency (RF) emitter or power source supplies energy at the appropriate power, frequency, and pulse shape to a RF applicator that in turn transmits pulses of RF energy into the subject or patient being imaged. The RF energy pulses transmitted into the subject stimulate the generation of thermoacoustic signals within the subject or patient that are received by the transducer. The received thermoacoustic signals in turn vibrate the piezoelectric element(s) of the thermoacoustic transducer causing the piezoelectric element(s) to convert the vibrations into an electrical potential. In response to the electrical potential, electrical pulses are conveyed to a data acquisition system that processes and transforms the electrical pulses into a digital image.

The RF energy pulses can directly affect the piezoelectric element(s) when emitted, creating false thermoacoustic data. The false thermoacoustic data is commonly referred to as an artifact(s). These artifacts interfere with actual thermoacoustic signals. Therefore in thermoacoustic imaging, there is a need to minimize artifacts from RF energy pulses.

SUMMARY

It should be appreciated that this summary is provided to introduce a selection of concepts in a simplified form that are further described below in the detailed description. This summary is not intended to be used to limit the scope of the claimed subject matter.

In one embodiment, a thermoacoustic transducer comprises: at least one piezoelectric element having a front surface and a rear surface; a potential electrode that is electrically connected to the rear surface; a ground electrode that is electrically connected to the front surface; a switch electrically connected to both the potential electrode and the ground electrode; a timer configured to match a pulse emanating from a radio-frequency emitter, further wherein the potential electrode and the ground electrode are electrically connected through an impedance when the switch is in an active state, further wherein the potential electrode and the ground electrode are not electrically connected when the switch is in an inactive state; and a housing accommodating the at least one piezoelectric element, potential electrode, ground electrode, and switch.

In one embodiment, the impedance is a resistor.

In one embodiment, the impedance is a combination of a resistor and an inductor.

In one embodiment, the impedance is a combination of a resistor, an inductor, and a capacitor.

In one embodiment, the pulse emanating from a radio-frequency emitter has a length of time between 0.1 nanoseconds and 10 microseconds.

In one embodiment, the pulse emanating from a radio-frequency emitter has a repetition rate 10 hertz and 2500 hertz.

In one embodiment, the switch is a single-pole double-throw switch.

In one embodiment, the switch is a combination of two single-pole single-throw switches.

In one embodiment, the timer is configured to activate the switch before the pulse emanates from the radio-frequency emitter.

In one embodiment, the timer is configured to deactivate the switch after the pulse stops emanating from the radio-frequency emitter.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including by not limited to" and the terms "comprising", "having" and "including" have equivalent meanings.

As used herein, the term "and/or" can include any and all combinations of one or more of the associated listed elements or features. Any embodiment described herein as "exemplary" is not necessarily to be construed as preferred or advantageous over other embodiments or designs and is intended to mean serving as an example, instance or illustration.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "rear", "back" and the like, may be used herein for ease of description to describe the relationship of an element or feature to another element or feature as illustrated in the figures. The spatially relative terms can however, encompass different orientations in use or operation in addition to the orientation depicted in the figures.

Figure 1:
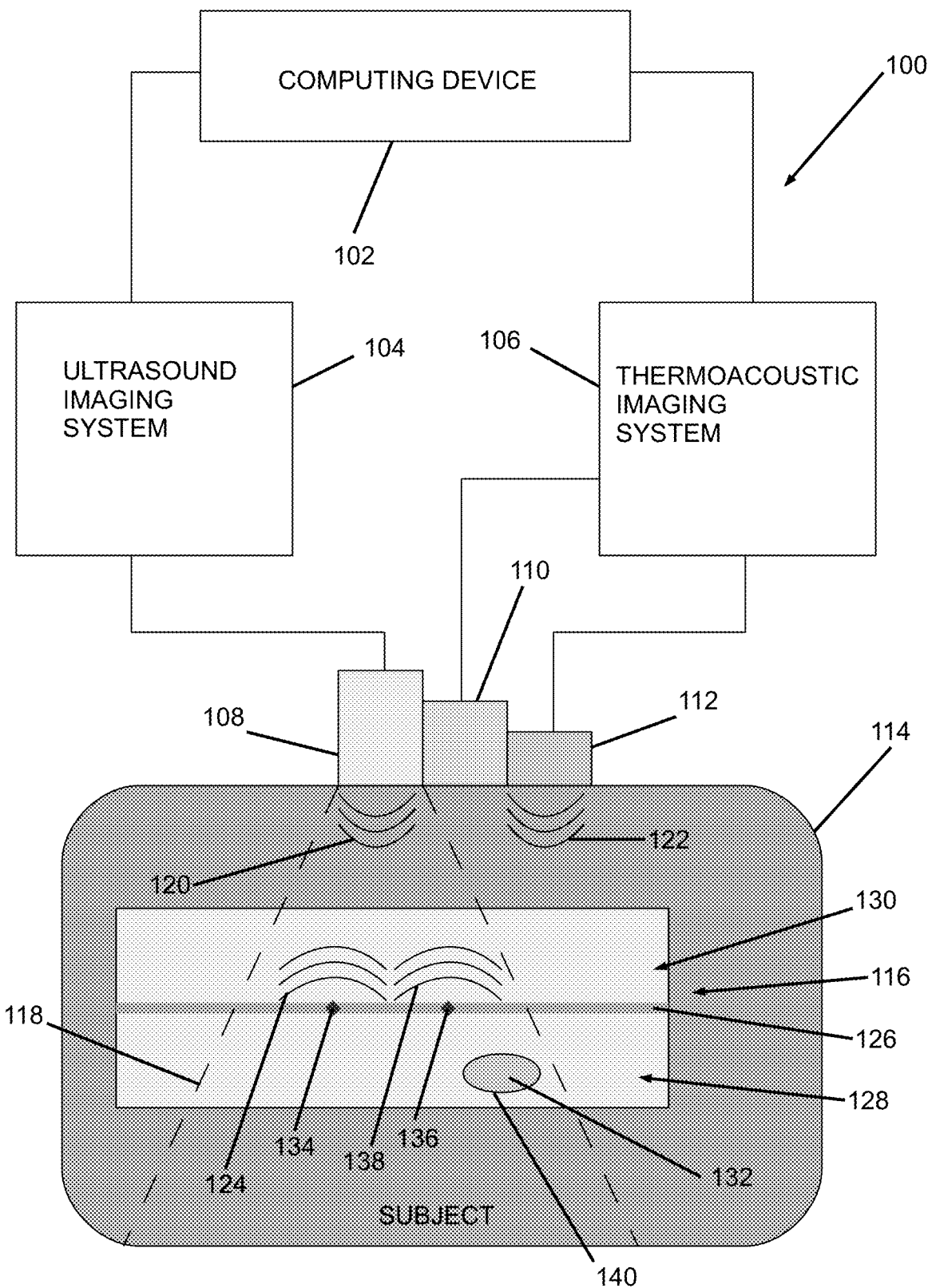
FIG. 1 schematically shows an imaging system embodiment.

Turning now to FIG. 1, an imaging system is shown and is generally identified by reference numeral 100. In this embodiment, the imaging system 100 comprises a computing device 102 communicatively coupled to an ultrasound imaging system 104 and a thermoacoustic imaging system 106. The ultrasound imaging system 104 and thermoacoustic imaging system 106 are configured to obtain ultrasound image data and thermoacoustic data, respectively, of a region of interest 116 associated within a subject 114. In the embodiment depicted in FIG. 1, the region of interest 116 comprises first reference 130, first boundary 126, second boundary 140, first boundary location 134, second boundary location 136, object of interest 128, and secondary object of interest (or tumor) 132.

The subject 114 can include a top surface 115, which may be skin. Components of the ultrasound imaging system 104 and the thermoacoustic imaging system 106 may be selectively coupled to the top surface 115 using gel-like material or a water capsule to interface to the subject.

The computing device 102 in this embodiment is a machine comprising a personal computer or other suitable processing device comprising, for example, a processing unit comprising one or more processors, non-transitory computer-readable memory (volatile and/or non-volatile memory), other non-removable or removable memory (e.g., a hard disk drive, RAM, ROM, EEPROM, CD-ROM, DVD, flash memory, etc.) and a system bus coupling the various computer components to the processing unit. The computing device 102 may also comprise networking capabilities using Ethernet, Wi-Fi, and/or other suitable network format, to enable connection to shared or remote drives, one or more networked computers, or other networked devices. One or more input devices, such as a mouse, stylus, touchscreen, and/or a keyboard (not shown) are coupled to the computing device 102 for receiving user input. A display device (not shown), such as a computer screen or monitor, can be coupled to the computer device 102 for displaying one or more generated images that are based on ultrasound image data received from the ultrasound imaging system 104 and/or the thermoacoustic data received from thermoacoustic imaging system 106.

The ultrasound imaging system 104 comprises one or more ultrasound transducer arrays 108 configured to emit sound waves 120 into the region of interest 116 of the subject 114. In this embodiment, the one or more ultrasound transducer arrays 108 are selectively connectable to the ultrasound imaging system 104. The sound waves 120 directed into the region of interest 116 of the subject 114 echo off tissue within the region of interest 116, with different tissues reflecting varying amount of sound. These echoes are received by the one or more ultrasound transducer arrays 108 and are processed by the ultrasound imaging system 104 before being communicated as ultrasound image data to the computing device 102 for further processing, and may be used for presentation and interpretation by an operator. In one embodiment, the ultrasound imaging system 104 utilizes B-mode ultrasound imaging techniques assuming a nominal speed of sound of 1,540 m/s. The B-mode image limits a field of view 118 of a conical shape extending from the ultrasound transducer arrays 108.

The thermoacoustic imaging system 106 comprises a processing unit comprising one or more processors, non-transitory system-readable memory (volatile and/or non-volatile memory), other non-removable or removable memory (e.g., a hard disk drive, RAM, ROM, EEPROM, CD-ROM, DVD, flash memory, etc.) and a system bus coupling the various system components to the processing unit. The thermoacoustic imaging system 106 also comprises at least one radio-frequency (RF) source 112 configured to generate short pulses of RF electromagnetic radiation that are directed into the region of interest 116 of the subject 114 to deliver energy to tissue within the region of interest 116 of the subject. The energy delivered to the tissue induces thermoacoustic pressure waves 124 and 138 that are detected by the thermoacoustic imaging system 106 using one or more thermoacoustic transducer arrays 110. The secondary object of interest (e.g., tumor) 132 also generates thermoacoustic pressure waves that are not shown in FIG. 1.

In one embodiment, the thermoacoustic imaging system 106 makes use of the one or more ultrasound transducer arrays 108 of the ultrasound imaging system 104 by disconnecting the one or more ultrasound transducer arrays 108 of the ultrasound imaging system 104 and connecting them to the thermoacoustic imaging system 106 and as such, coordinate mapping between ultrasound transducer arrays 108 is not required.

In one embodiment, the RF source 112 has a frequency between about 10 MHz and 100 GHz and has a pulse duration between about 0.1 nanoseconds and 10 microseconds. Acoustic pressure waves detected by the one or more thermoacoustic transducer arrays 110 are processed and communicated as thermoacoustic data to the computing device 102 for further processing, and may be used for presentation and interpretation by an operator.

In a separate embodiment, the thermoacoustic imaging system 106 could utilize separate thermoacoustic transducers from the ultrasound transducer arrays 108. Each transducer may have one or more transducer elements. Transducer elements may have the same specifications (e.g., center frequency), but other aspects may vary (e.g., bandwidth).

In one embodiment, a user utilizes the computing device 102 to operate the ultrasound imaging system 104. The ultrasound imaging system 104 sends a signal to ultrasound transducer arrays 108, which sends sound waves 120 into subject 114 (the ultrasound transducer arrays 108 typically rest on the skin 115 of the subject (e.g., patient). The sound waves 120 reflect off of objects within the subject 114 and the ultrasound transducer arrays 108 receive the reflected sound waves to generate a B-mode image via the ultrasound imaging system 104. The extent of the B-mode image is a conic section and is shown with B-mode image limits 118.

The B-mode image gives the physical location of the region of interest 116 and boundary 126, enabling the computing device 102 to correlate data from the thermoacoustic imaging system 106 via the actual position on the subject 114 of the thermoacoustic transducer array 110 and RF emitter 112. Typically, once position coordinates are known, the ultrasound imaging system 104 can be turned off to eliminate potential interference with the thermoacoustic imaging system 106. The thermoacoustic imaging system 106 then initiates the RF emitter 112 to send RF energy pulses 122 into the subject 114. The RF energy 122 pulses are absorbed in the region of interest 116. Within the region of interest 116, there are boundaries 126 and 140 between references 130 and an object of interest 128. The difference between RF energy absorbed in reference 130 and object of interest 128 creates thermoacoustic multipolar signals 124 and 138 emanating from boundary locations 134 and 136. Thermoacoustic transducer array 110 receives the thermoacoustic multipolar signals 124 and 138 and sends the resulting data to the thermoacoustic imaging system 106, which can share the data with the computing device 102.

The processes described below may be implemented using the hardware described with respect to FIG. 1. The processes may be performed by the computing device 102, thermoacoustic imaging system 106, or a combination of the computing device 102 and thermoacoustic imaging system 106. For example, a simulation and configuration of the transducer geometry can be performed using the computing device 102 or the thermoacoustic imaging system 106.

Figure 2:
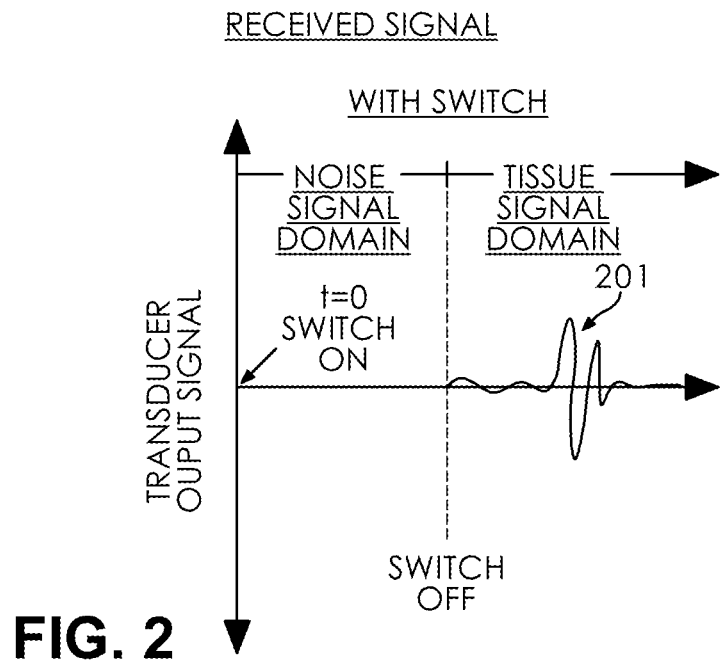
FIG. 2 shows a received signal from an imaging system with a switch, according to embodiments.
Figure 4A:
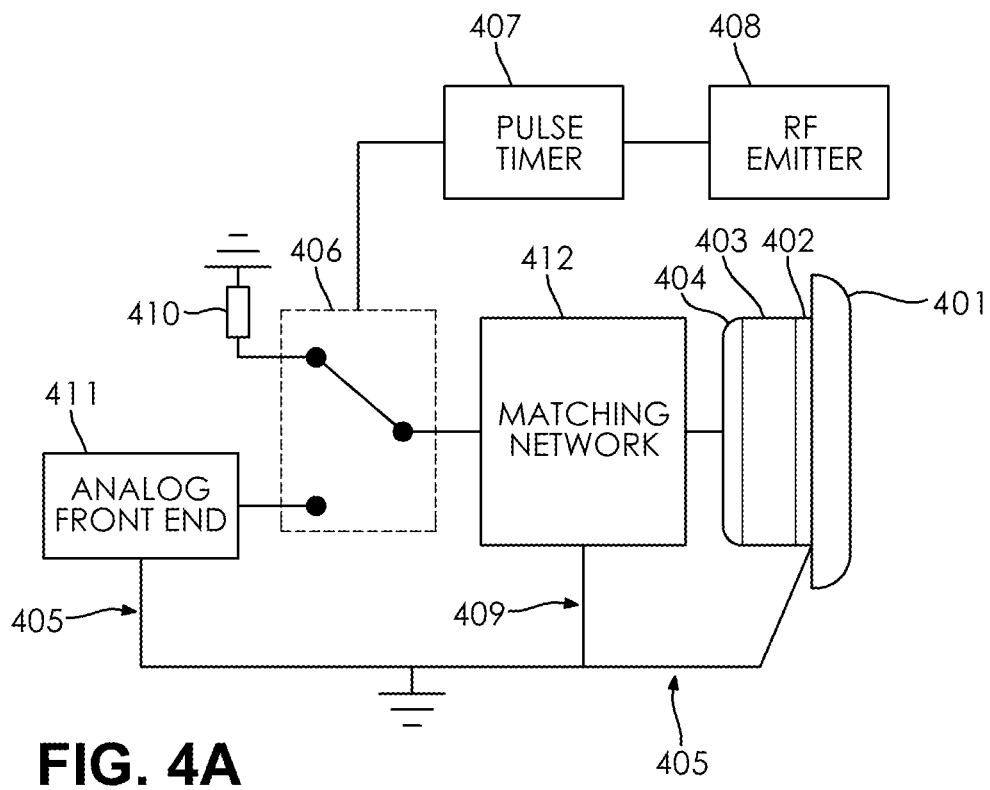
FIG. 4A shows an imaging system schematic with an activated switch, according to embodiments.
Figure 4B:
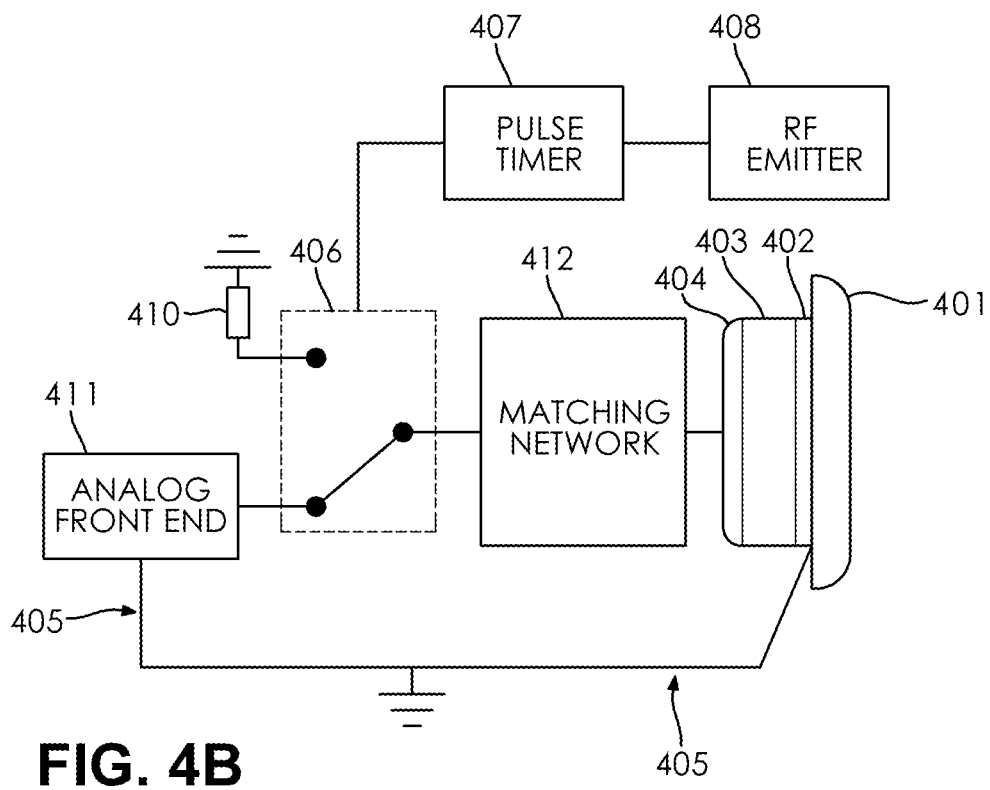
FIG. 4B shows an imaging system schematic with an inactivated switch, according to embodiments.

FIG. 2 shows a received signal from an exemplary imaging system 106 with a switch 406, shown as exemplary in FIGS. 4A and 4B. With the switch 406 on (activated, as shown in FIG. 4A), the thermoacoustic imaging system 106 receives a reduced (dampened) signal during the noise signal domain. With the switch 406 off (deactivated, as shown in FIG. 4B), the thermoacoustic imaging system 106 receives a thermoacoustic signal, 124 and 136, from the region of interest 116 during the tissue signal domain. The noise (artifact) from the emitted RF pulse 122 directly impacting the piezoelectric element 402 is mitigated during the noise signal domain, with energy from the noise from the emitted RF pulse 122 being shunted into the impedance 410. The resulting signal 201 is shown.

Potential switch 406 embodiments include, but are not limited to: analog-based switches, digital-based switches, diode-based switches, MOSFET-based switches, transistor-based switches, mechanical relay(s), solid state relay(s), logic-based switches, some combination thereof, or the like.

Potential matching network embodiments include but are not limited to: high voltage protection circuits (in some cases based upon clamping diodes), impedance matching circuits, some combination thereof, or the like.

Figure 3:
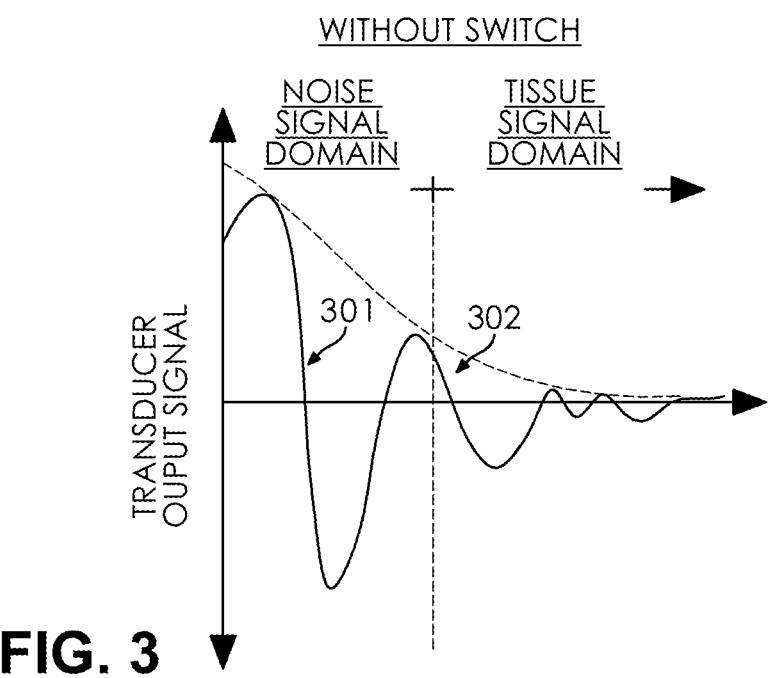
FIG. 3 shows a received signal from an imaging system without a switch, according to embodiments.

FIG. 3 shows an exemplary received signal (or output signal) from an embodiment of the imaging system 106 without a switch. The thermoacoustic imaging system 106 receives an artifact signal 301 (noise) during the noise signal domain. The thermoacoustic imaging system 106 receives both a thermoacoustic signal, 124 and 136, from the region of interest 116 during the tissue signal domain and the remaining artifact signal 302 (noise). Hence, the noise is mitigated in FIG. 2 but not mitigated in FIG. 3.

FIG. 4A schematically shows an exemplary imaging system 106 having a switch 406 in an activated state. Shown are sensor face 401, piezoelectric element 402, backing material 403, acoustic insulator 404, ground wire 405, switching element (switch) 406, pulse timer 407, RF emitter 408, optional matching network ground wire 409, impedance 410, and analog front end module 411. Thermoacoustic signals and other vibrations from outside the region of interest 116 strike sensor face 401 and a mechanical force is absorbed at a front surface of piezoelectric element 402. The piezoelectric element 402 converts the mechanical energy to electrical energy, which travels from piezoelectric element 402 to matching network module 412 (through backing material 403 and acoustic insulator 404 via a wire that partially hidden (shown between acoustic insulator 404 and matching network module 412 but hidden in backing material 403 and acoustic insulator 404)). The matching network 412 is calibrated to match a desired impedance, such as the impedance of human skin. Electrical energy travels through the matching network module 412, then through additional impedance 410, to then be shunted to ground. This occurs during noise signal domain, as shown in FIG. 2.

FIG. 4B schematically shows an exemplary imaging system 106 having a switch 406 in an inactivated state. Shown are sensor face 401, piezoelectric element 402, backing material 403, acoustic insulator 404, ground wire 405, switching element (switch) 406, pulse timer 407, RF emitter 408, optional matching network ground wire 409, impedance 410, and analog front end module 411. Thermoacoustic signals and other vibrations from outside the region of interest 116 strike sensor face 401 and a mechanical force is absorbed at a front surface of piezoelectric element 402. The piezoelectric element 402 converts the mechanical energy to electrical energy, which travels from piezoelectric element 402 to matching network module 412 (through backing material 403 and acoustic insulator 404 via a wire that partially hidden (shown between acoustic insulator 404 and matching network module 412 but hidden in backing material 403 and acoustic insulator 404)). The matching network 412 is calibrated to match a desired impedance, such as the impedance of human skin. Electrical energy travels through the matching network module 412, then through additional analog front end module 411. This occurs during tissue signal domain, as shown in FIG. 2 and FIG. 3.

Matching network module 412 is connected between the piezoelectric element 402 and the load. The load is either the analog front end module 411 or the impedance 410 connected to ground depending on the state of the switching element 406. The matching network module 412 transforms the output impedance of the transducer such that it is equal to the complex conjugate of the load impedance, enabling preferential power transfer from the transducer to the load.

Figure 5:
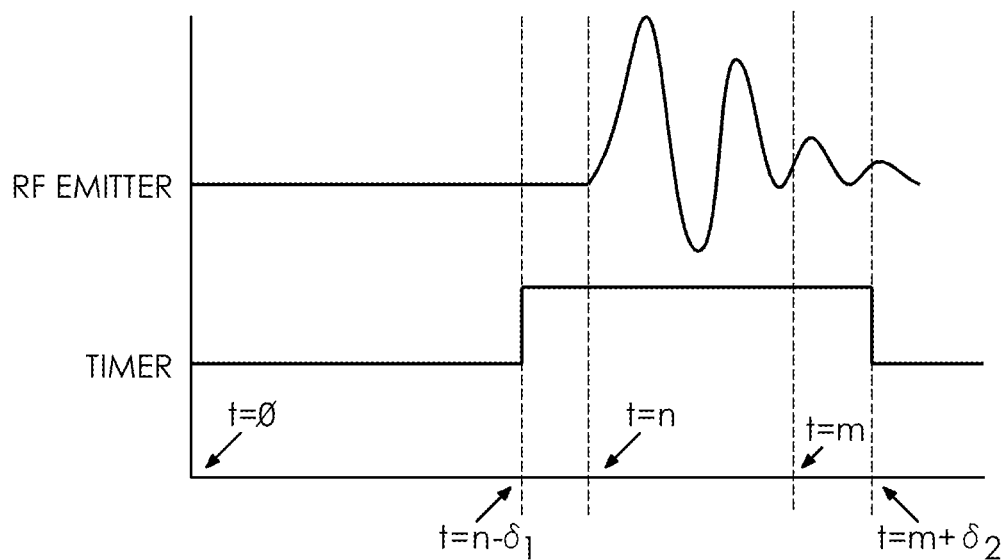
FIG. 5 shows an exemplary timing diagram, with the timer activated before the pulse and the timer deactivated after the pulse.

FIG. 5 shows an exemplary timing diagram, with the timer activated before the pulse and the timer deactivated after the pulse. RF emitter 408 emits RF pulses 122 from time t=n to time t=m. The acoustic noise (artifacts) generated from the RF pulses 122 are shown as the RF EMITTER plot in FIG. 5. The acoustic noise (artifacts) begin at t=n and begin to decline after in amplitude after t=m. The acoustic noise (artifacts) are shown as a baseline (offset from zero) with both positive and negative fluctuations.

In the FIG. 5 embodiment, pulse timer 407 initiates (is activated, turns on) before the RF emitter 408 begins emitting RF pulses 122 and deactivates (turns off) after the RF emitter 408 stops emitting RF pulses 122. The activation states of the pulse timer 407 are shown as the TIMER plot in FIG. 5, with deactivates (off) being the lower state and activated (on) being the upper state. In one embodiment, pulse timer 407 transmits a discrete step change signal (e.g., 5 volts).

Figure 6:
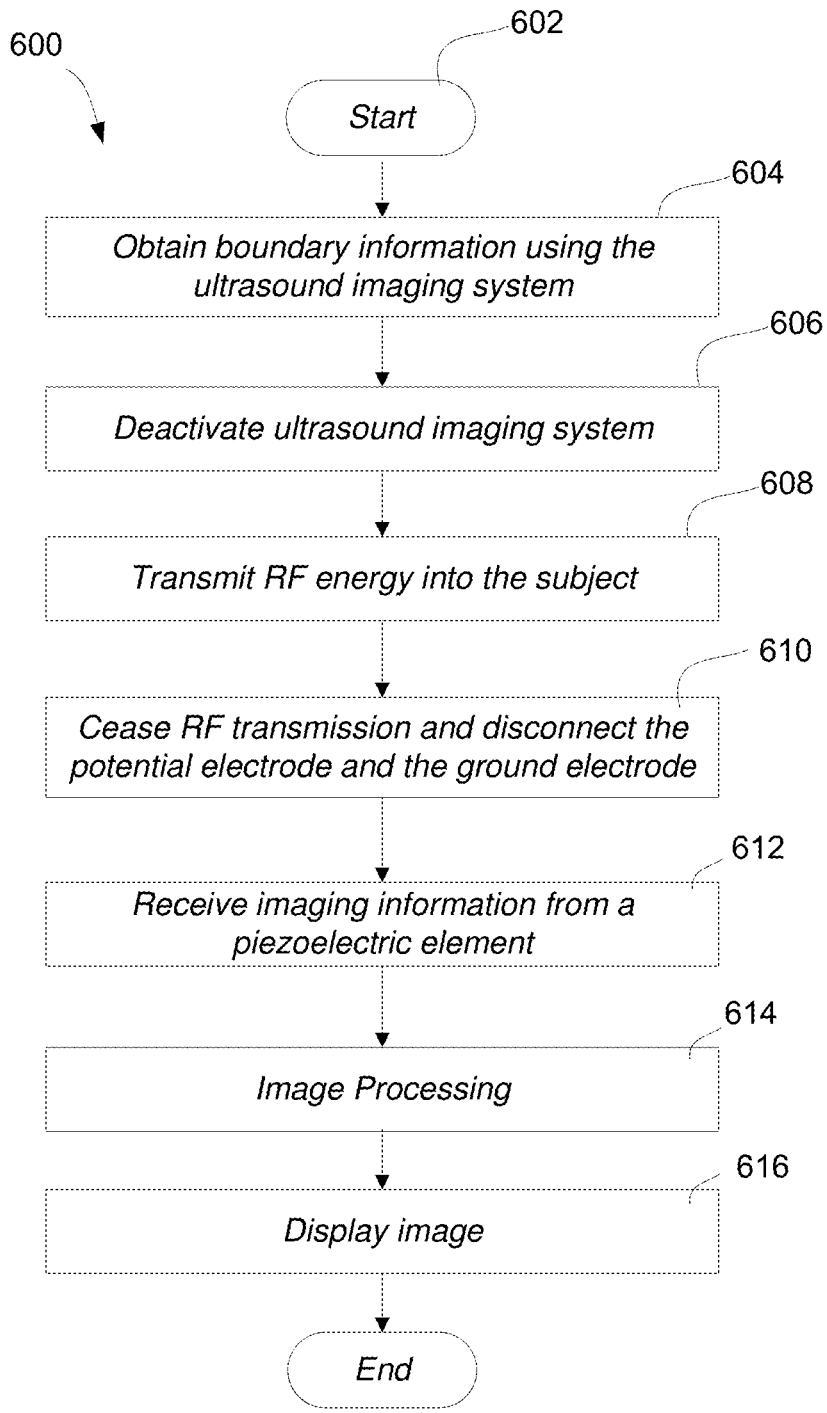
FIG. 6 for shows an exemplary process for receiving a signal from an imaging system, according to embodiments.
Figure 1:
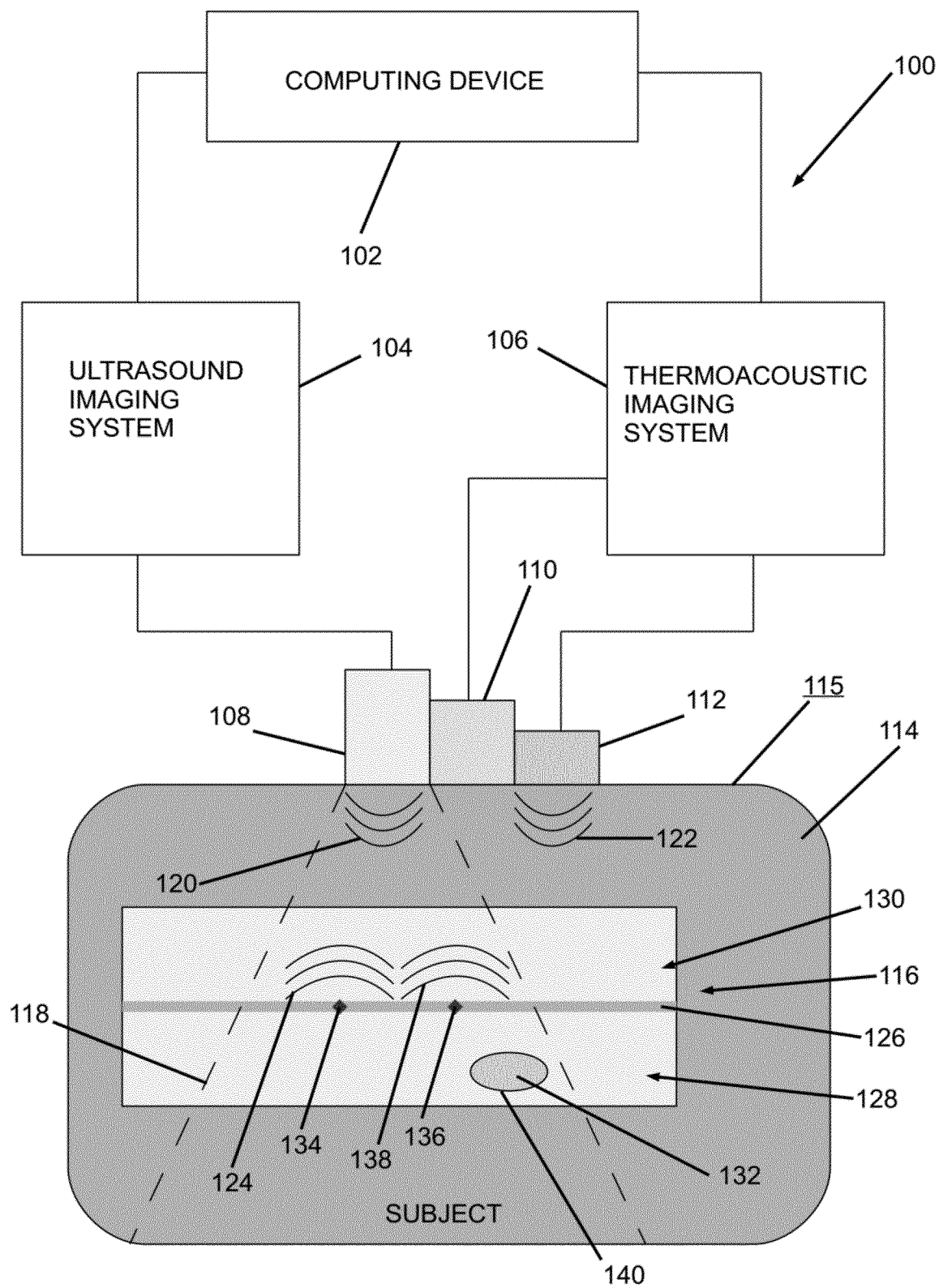

FIG. 6 shows an exemplary process 600 for reducing artifacts from echoed RF energy pulses within a subject using an exemplary imaging system 100. As FIG. 6 shows, the process 600 may be initialized manually or automatically in accordance with other executing processes. In one embodiment, the process 600 is initialized by simply turning the system 100 to an ON operating state. In one embodiment, the process 600 is initialized by receiving instructions from a computer program or operator to start 602.

At step 604, the imaging system 100 obtains boundary information from the ultrasound imaging system 104. As described hereinabove, the ultrasound imaging system 104 emits sound waves 120 into the region of interest 116 of the subject 114 via the ultrasound transducer arrays 108. Echoes from the sound waves are received by the one or more ultrasound transducer arrays 108 and are processed by the ultrasound imaging system 104 to determine the region of interest 116 and a boundary 126. The region of interest 116 and/or the boundary 126 can be used by the system 100 to correlate data from the thermoacoustic imaging system 106.

At step 606, the ultrasound imaging system 104 can be deactivated to eliminate potential interference with the thermoacoustic imaging system 106.

At step 608, the thermoacoustic imaging system 106 then initiates the RF emitter 112 to send RF energy pulses 122 into the subject 114. The RF energy 122 pulses are absorbed in the region of interest 116 as described hereinabove. The switch 406 electrically connects the potential electrode and the ground electrode when the radio-frequency emitter 112 is in an active state. In one embodiment, an impedance is connected in series between the potential electrode and the ground electrode.

At step 610, the system 100 can concurrently, or nearly concurrently, cease RF energy transmission into the subject and electrically disconnect the potential electrode and the ground electrode via the switch 406. In one embodiment, the switch 406 connects the piezoelectric element 402 to the analog front end module 411 in series upon electrically disconnecting the potential electrode and the ground electrode.

At step 612, the system 100 receives imaging information via the thermoacoustic transducer array 110 receives the thermoacoustic multipolar signals 124 and 138 and sends the resulting data to the thermoacoustic imaging system 106.

At step 614, the system 100 may execute signal conditioning techniques and image processing on the received imaging information.

At step 616, the system 100 displays the image.

The schematic flow chart diagram is included herein to generally set forth as a logical flow chart diagram. As such, the depicted order and labeled steps are indicative of one embodiment of the presented process. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the process. For example, an arrow may indicate a waiting or monitoring period of unspecified duration between enumerated steps of the depicted process. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Additionally, the order in which a particular method occurs may or may not strictly adhere to the order of the corresponding steps shown. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures. For example, steps 610, 612, 614, and 616 may be executed concurrently in some embodiments.

As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of computer readable program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of computer readable program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the computer readable program code may be stored and/or propagated on in one or more computer readable medium(s). In the context of this document, a computer readable storage medium may be any tangible medium that can contain, and/or store computer readable program code for use by and/or in connection with an instruction execution system, apparatus, or device.

Computer readable program code for carrying out operations for aspects of the present invention may be written in any combination of one or more programming languages. The computer readable program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Although embodiments have been described above with reference to the accompanying drawings, those of skill in the art will appreciate that variations and modifications may be made without departing from the scope thereof as defined by the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

What is claimed is:

1. A thermoacoustic system comprising a radio-frequency emitter adjacent to a thermoacoustic transducer, the thermoacoustic transducer comprising:
   a transducer element having a first surface and a second surface;
   a switch electrically connected to the transducer element through a matching network, wherein the switch is electrically connected to a ground through an impedance when the switch is in an active state, further wherein the switch is electrically connected to an analog front end when the switch is in an inactive state; and
   a pulse timer configured to place the switch in an active state when energy is emanating from the radio-frequency emitter and place the switch in an inactive state when energy is not emanating from the radio-frequency emitter.

2. The thermoacoustic transducer of claim 1, wherein the impedance is a resistor.

3. The thermoacoustic transducer of claim 1, wherein the impedance is a combination of a resistor and an inductor.

4. The thermoacoustic transducer of claim 1, wherein the impedance is a combination of a resistor, an inductor, and a capacitor.

5. The thermoacoustic transducer of claim 1, wherein a guise emanating from the radio-frequency emitter has a length of time between 0.1 nanoseconds and 10 microseconds.

6. The thermoacoustic transducer of claim 1, wherein a pulse emanating from the radio-frequency emitter has a repetition rate between 10 hertz and 2500 hertz.

7. The thermoacoustic transducer of claim 1, wherein the switch is a single-pole double-throw switch.

8. The thermoacoustic transducer of claim 1, wherein the switch is a combination of two single-pole single-throw switches.

9. The thermoacoustic transducer of claim 1, wherein the pulse timer is configured to activate the switch before a pulse emanates from the radio-frequency emitter.

10. The thermoacoustic transducer of claim 1, wherein the pulse timer is configured to deactivate the switch after a pulse stops emanating from the radio-frequency emitter.

* * * * *

UNITED STATES PATENT AND TRADEMARK OFFICE
CERTIFICATE OF CORRECTION

| | | |
|---|---|---|
| PATENT NO. | : 11,172,829 B2 | |
| APPLICATION NO. | : 17/230480 | |
| DATED | : November 16, 2021 | |
| INVENTOR(S) | : Zackary Marc Mumm et al. | |

It is certified that error appears in the above-identified patent and that said Letters Patent is hereby corrected as shown below:

In the Drawings

Please replace Fig. 1 with Fig. 1 as shown on the attached page

In the Specification

Column 2, Line 9 should read: frequency emitter has a repetition rate between 10 hertz and 2500
Column 2, Line 40 should read: FIG. 6 shows an exemplary process for receiving a
Column 3, Line 31 should read: region of interest 116 associated with a subject 114. In the
Column 5, Line 11 should read: into the subject 114. The RF energy pulses 122 are absorbed
Column 5, Line 37 should read: a thermoacoustic signal, 124 and 138, from the region of
Column 5, Line 58 should read: both a thermoacoustic signal, 124 and 138, from the region
Column 6, Line 2 should read: signals and other vibrations from the region of
Column 6, Line 12 should read: module 412 is calibrated to match a desired impedance, such as the
Column 6, Line 24 should read: moacoustic signals and other vibrations from the
Column 6, Line 34 should read: matching network module 412 is calibrated to match a desired
Column 6, Line 54 should read: begin to decline in amplitude after t=m. The acoustic
Column 7, Line 25 should read: into the subject 114. The RF energy pulses 122 are absorbed
Column 8, Line 60 should read: stored and/or propagated in one or more computer In the Claims Column 9, Line 23-Column 10, Line 32 should be corrected to read:
1. A thermoacoustic system comprising a radio-frequency emitter adjacent to a thermoacoustic transducer, the thermoacoustic transducer comprising:
    a transducer element having a first surface and a second surface;
    a switch electrically connected to the transducer element through a matching network, wherein the switch is electrically connected to a ground through an impedance when the switch is in an active state, further wherein the switch is electrically connected to an analog front end when the switch is in an inactive state; and Signed and Sealed this
Twenty-third Day of May, 2023

*Katherine Kelly Vidal*
Katherine Kelly Vidal
*Director of the United States Patent and Trademark Office* a pulse timer configured to place the switch in an active state when energy is emanating from the radio-frequency emitter and place the switch in an inactive state when energy is not emanating from the radio-frequency emitter.

2. The thermoacoustic system of claim 1, wherein the impedance is a resistor.

3. The thermoacoustic system of claim 1, wherein the impedance is a combination of a resistor and an inductor.

4. The thermoacoustic system of claim 1, wherein the impedance is a combination of a resistor, an inductor, and a capacitor.

5. The thermoacoustic system of claim 1, wherein a pulse emanating from the radio-frequency emitter has a length of time between 0.1 nanoseconds and 10 microseconds.

6. The thermoacoustic system of claim 1, wherein a pulse emanating from the radiofrequency emitter has a repetition rate between 10 hertz and 2500 hertz.

7. The thermoacoustic system of claim 1, wherein the switch is a single-pole double-throw switch.

8. The thermoacoustic system of claim 1, wherein the switch is a combination of two single-pole single-throw switches.

9. The thermoacoustic system of claim 1, wherein the pulse timer is configured to activate the switch before a pulse emanates from the radio-frequency emitter.

10. The thermoacoustic system of claim 1, wherein the pulse timer is configured to deactivate the switch after a pulse stops emanating from the radio-frequency emitter.